United States Patent [19]

Miller

[11] 4,427,012

[45] Jan. 24, 1984

[54] ENEMA APPARATA IMPROVEMENTS RELATING TO DOUBLE CONTRAST STUDIES

[76] Inventor: Roscoe E. Miller, 7400 West 88th St., Indianapolis, Ind. 46278

[21] Appl. No.: 470,247

[22] Filed: Mar. 30, 1983

Related U.S. Application Data

[60] Division of Ser. No. 347,900, Feb. 11, 1982, which is a continuation-in-part of Ser. No. 131,965, Apr. 4, 1980, Pat. No. 4,333,460, which is a continuation-in-part of Ser. No. 39,502, May 16, 1979, abandoned.

[51] Int. Cl.³ .............................................. A61B 5/00
[52] U.S. Cl. ........................................ 128/654; 604/45
[58] Field of Search .................... 128/654; 604/27, 28, 604/30–34, 39, 43, 45

[56] References Cited

U.S. PATENT DOCUMENTS

| | | | |
|---|---|---|---|
| 1,740,240 | 12/1929 | Honey | 604/45 X |
| 3,208,145 | 9/1965 | Turner | 604/45 |
| 4,074,709 | 2/1978 | Kaplan | 128/654 |
| 4,299,221 | 11/1981 | Phillips et al. | 604/45 |

Primary Examiner—John D. Yasko
Attorney, Agent, or Firm—Woodard, Weikart, Emhardt & Naughton

[57] ABSTRACT

An enema administering apparatus insertable into the rectum for delivery of a contrast medium to internal portions of a patient's anatomy includes an enema tip wherein the enema tip has a contrast medium passageway extending therethrough and is able to be coupled through the use of a disclosed adapter to a source of contrast medium. Also disclosed in various arrangements is an air passageway which is exterior of the contrast medium passageway and is able to be coupled to a source of air for double contrast studies. The air passageway may be a passageway disposed within the enema tip construction or may be a separate tubing member joined therewith in a suitable arrangement to introduce air for the double contrast studies once the barium has been evacuated from the patient. Also disclosed are air valve means that close the air passageway to the flow of barium in one direction yet open for the flow of air in the opposite direction.

3 Claims, 40 Drawing Figures

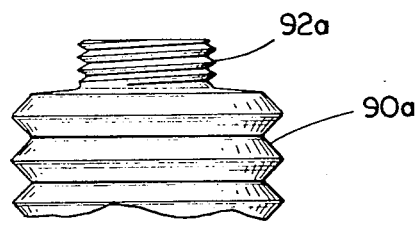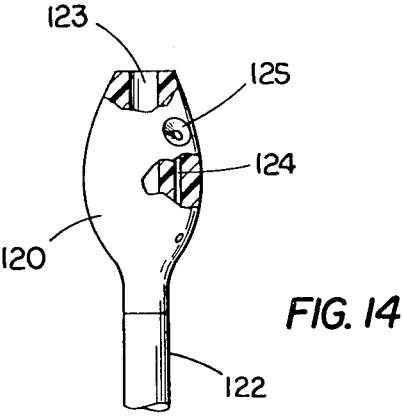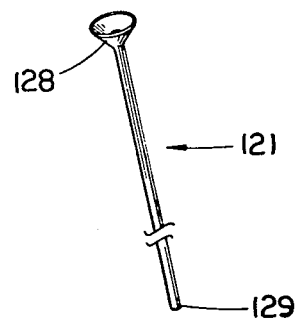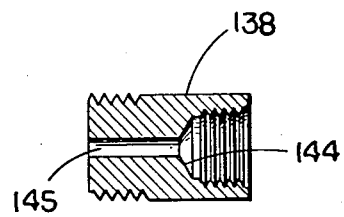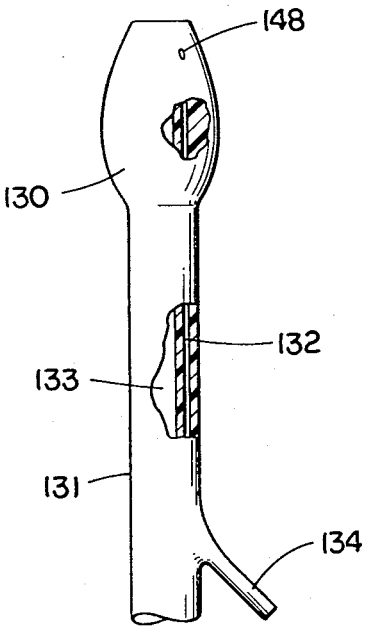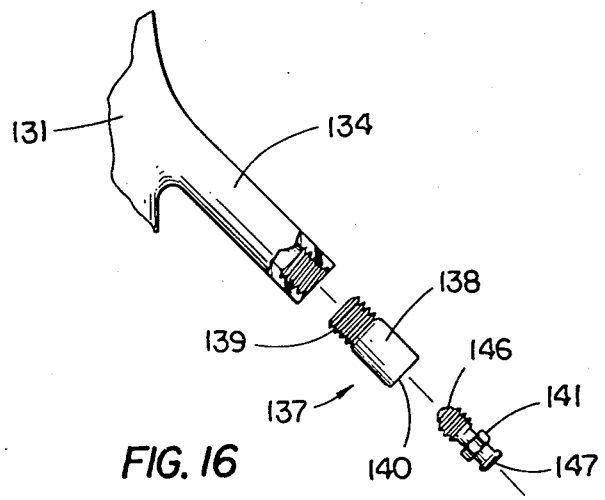

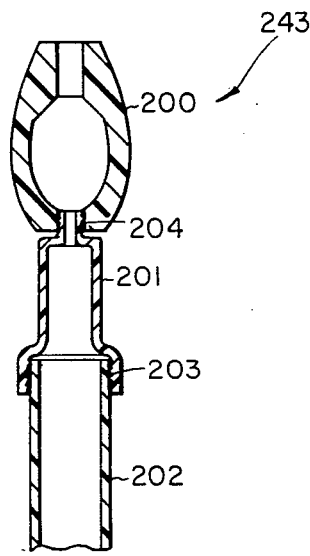
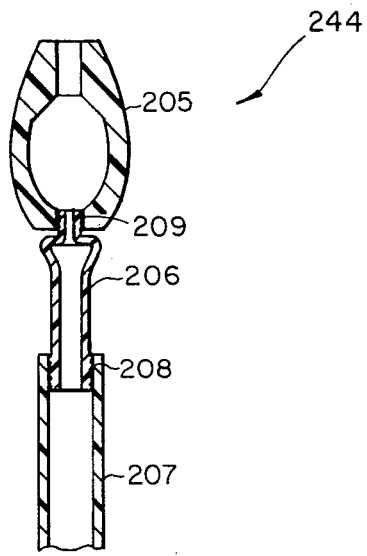
FIG.25  FIG.26
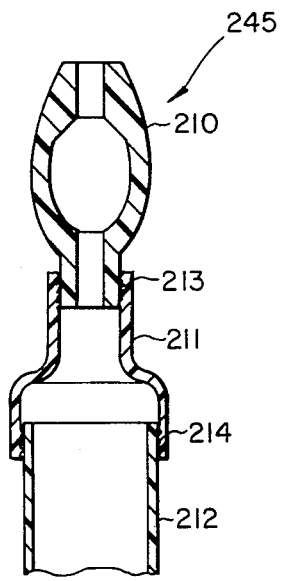
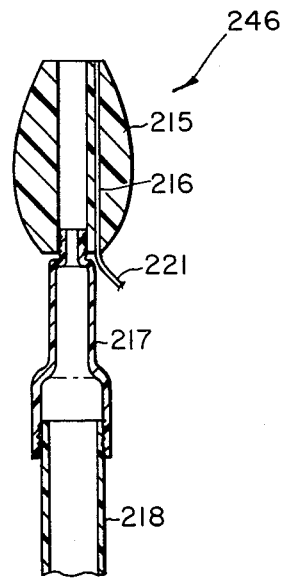
FIG.27  FIG.28

ENEMA APPARATA IMPROVEMENTS RELATING TO DOUBLE CONTRAST STUDIES

REFERENCE TO RELATED APPLICATION

This application is a division of application Ser. No. 347,900, filed Feb. 11, 9182, which is a continuation-in-part patent application of my prior copending patent application Ser. No. 131,965 filed Apr. 4, 1980, now U.S. Pat. No. 4,333,460 which application is a continuation-in-part patent application of Ser. No. 39,502 filed May 16, 1979 now abandoned.

BACKGROUND OF THE INVENTION

This invention relates in general to enema administering procedures and apparata and in particular to enema tip improvements and administering techniques associated with double contrast studies.

Enema administering apparata are often used to control the rectal introduction of a contrast medium such as barium for such procedures as X-ray examination of the colon. While a variety of problems may be encountered with incontinent patients, one problem involves the inability of such patients to retain the enema tip during a fluoroscopy examination. Various solutions to this problem have been provided by the improved enema administering apparata disclosed in my copending patent application, Ser. No. 39,280, filed on May 16, 1979.

Another problem which is applicable to virtually all patients is the time lapse between preevacuation and postevacuation X-ray films when an air contrast study is required. Frequently referred to as a "double contrast" enema or fluoroscopy procedure, such a routine involves a conventional barium enema first, followed by an injection of air once the barim is evacuated. X-ray films are taken just prior to evacuation, air is then injected and postevacuation X-ray films are taken. An undue elapse of time between the preevacuation and postevacuation films allows the barium to dehydrate partially on the walls of the bowel when the air is injected. This results in highly unsatisfactory radiographs. Therefore, it would be an improvement to the various apparata currently used, as well as the procedures presently followed, if means were available for a rapid evacuation and prompt injection of air.

With currently used air-contrast apparata and procedures, the enema tube and tip are used for both the barium as well as for the air, and there is normally a separate air tube or passageway which is coupled to air introducing means. One problem with such an arrangement is that the air tube extends through the barium (or other contrast medium) passageway and partially blocks or impedes the flow of medium (barium). Furthermore, if suction is used for evacuation via the contrast medium passageway, some of the contrast medium may clog the air tube. Therefore, it would be an improvement to provide an air tube or air passageway as part of an enema tube and tip which does not interfere with the introduction of the contrast medium into the patient nor become clogged upon contrast medium evacuation.

This improvement can be accomplished by suitably spacing the contrast medium passageway and air tube so that the evacuation of contrast medium would not cause significant flow of contrast medium around or into the air tube.

Avoidance of clogging of the air tube can also be accomplished by providing a suitable type of valve which keeps the air tube shut while the contrast medium is being evacuated. This valve then allows the passage of air into the patient.

This valve function can be accomplished by the use of a damper with a living hinge which is in a normally closed condition and disposed over the air outlet opening. This damper precludes the flow of contrast medium into the air passageway during the evacuation procedure. Subsequently, the force of the air flowing through the air passageway pushes the damper open as it pivots about its living hinge. Another style of valve suitable for use is a ball valve. Still another style of valve means suitable for use are normally closed flexible lips. These lips may be disposed as part of the enema tip or alternatively as part of the air tube. The introduced air flow forces the lips open thus allowing the flow of air into the patient.

The foregoing valve means concept overcomes those problems associated with prior art introduction means. A simple flap can be used for a valve and when disposed in a normally closed condition precludes the entry of barium into the air passageway. The beauty of this idea is that existing enema tips can be retrofitted with such valves and thereby become suitable for successful double contrast studies.

Another problem with some presently used enema apparata is the lack of uniformity in tubing size for the tubing that is used to connect the tip with the enema bag. To alleviate this problem, an adapter can be used to interface directly between a standard sized tip and a variable-sized enema bag tubing. In this way, a simple, inexpensive set of adapters can be stored and used to easily and conveniently couple the enema tip directly to any size of tubing that is provided with the enema bag.

Another problem which often occurs involves the size and length of the enema-administering apparatus. Usually the apparatus includes a six foot long enema tube which connects the enema tip with the barium bag. These long lengths of tubing are cumbersome, and cause a great deal of barium to be wasted, because some of the barium remains in the tubing. The long tubing also tends to develop kinks which may restrict the flow of barium. A related concern is the size of the enema bag that holds the barium. A large barium bag has to be used because barium is wasted by just filling the long tubes. For these reasons, a shorter tube and a smaller bag would provide for efficiency, ease of use and patient comfort.

A related problem with present apparata is that someone has to hold the barium bag below the level of the patient's bowels in order to allow for the barium to drain out of the patient during the evacuation step. With the longer lengths of tubing, the bag is usually placed on the floor. With slightly shorter lengths, the patient has to hold the bag. Because this is awkward and many patients tend to be older, this approach is not really acceptable. Therefore, means are needed so that the bag can be secured at some point sufficiently below the patient's rectum so as to achieve proper drainage. One way to achieve this is provide a strap as part of the barium bag which is then tied around the patient's leg. A belt tied around the patient's waist with a hanging strap with notches in it can also be used. The barium bag is then hung on the appropriate notch at an appropriate height.

The use of a smaller bag and shorter tube also allows for the use of the bag as means for shipping premixed barium within the actual bag. This will eliminate the necessity of preparing the bag initially. Smaller bags would also be less expensive to ship.

There are various enema-related apparata which have been conceived as set forth by the disclosures of the following listed patents. However, none of these disclosures set forth a device with advantages equal to the advantages of the present invention to be described in detail hereinafter. Thus, the present invention is an improvement to all prior art devices of which the inventor is aware.

| Pat. No. | Patentee | Issue Date |
| --- | --- | --- |
| 4,117,847 | Clayton | 10/03/78 |
| 3,707,146 | Cook et al. | 12/26/72 |
| 3,766,920 | Greene | 10/23/73 |
| 3,788,328 | Alley et al. | 1/29/74 |
| 4,090,502 | Tajika | 5/23/78 |
| 3,509,884 | Bell | 5/05/70 |
| 3,078,848 | Milbert | 2/26/63 |
| 3,769,962 | McVey | 11/06/73 |
| 4,044,757 | McWhorter et al. | 8/30/77 |
| 3,915,152 | Colonna | 10/28/75 |
| 3,760,805 | Higuchi | 9/25/73 |
| 3,752,146 | Kline | 8/14/73 |
| 3,844,284 | Schoenfeld et al. | 10/29/74 |
| 4,068,662 | Sneider | 1/17/78 |
| 4,014,332 | Sneider | 3/29/77 |
| 3,459,175 | Miller | 8/05/69 |
| 3,375,823 | Pamplin et al. | 4/02/68 |
| 2,112,160 | Johnson | 3/22/38 |

Clayton discloses improvements in colon catheters for removing waste colon materials and includes a hollow main tube which is insertable into the anal opening and is held therein by an inflatable member located within the anal opening and by limiting elements located outside of the anal opening and extending for and aft from the main tube. An irrigation tube or the like is provided for directing enema fluid into the rectum above the inserted catheter.

Cook et al. discloses a means to inject a plastic into a cavity to produce a replica thereof and is particularly suitable to produce a soft resilient plastic impression of the interior configuration of a body cavity. An air bulb is provided and connected to the injection syringe by a section of tubing wherein the tubing exits at an inflatable cuff which is used to prevent inadvertent withdraw of the catheter during the injection operation.

Greene discloses a smooth, flexible enema tip having an inflatable balloon mounted on the stem behind the exit port from the tip. A limited volume, flexible hand distendable air reservoir is connected to the balloon-like retention ring so that operator compression of the reservoir will inflate the ring.

Alley et al. discloses a cardiovascular catheter for use particularly in open-heart surgery and related operations requiring varying forms of cardiopulmonary by-pass. The catheter has a fixed ring provided on the catheter proximal to drainage inlets and may have a sliding ring snug fit on the catheter proximal to the fixed ring for securing the catheter to a penetrated portion of the anatomy, such as the heart wall, between the two rings to assist in holding the catheter in place.

Tajika discloses a remote-controlled barium injection apparatus for the injection of barium into the lower digestive tract of a patient to be examined and for the subsequent reflux and evacuation of the barium by air compression. The objective is to create greater safety in the production of double contrast studies or fluoroscopic examination. The apparatus employs detachable and insert units which are the only portion of the apparatus in direct contact with a patient.

Bell discloses a rectal balloon catheter with inflatable stop or limit means for limiting the depth of insertion of the catheter into a body cavity to a predetermined maximal depth.

Milbert discloses a medical applicator which includes a multiple-position valve disposed in line between three tubing sections. One section of tubing couples to a fluid bag and the other two sections of tubing extend to remote use locations for this fluid. By selective positioning of the valve component, the fluid may be coupled to one or the other of the two remote use locations or may be closed off completely.

McVey discloses a barium enema administration method and apparatus which includes a three-way union of conduits, one conduit is connected to a gravity feed barium supply source, another conduit is connected to a source of air under pressure and the last conduit is an evacuation line connected to a source of suction. Each conduit is controlled by an individual valve and the valves are opened and closed in a prescribed sequence as directed by the radiologist.

McWhorter discloses a device for use in cholangiography and similar procedures comprising, a first syringe having a barrel defining a chamber for retaining an irrigation liquid and a plunger having one end received in the chamber for pumping the liquid from the chamber. The device has a second syringe having a barrel defining a chamber for retaining a liquid contrast medium and a plunger having one end received in the chamber of the second syringe for pumping the contrast medium from the chamber. The two syringes are jointly coupled to a catheter and this union may be provided with a selectably positionable valve.

Colonna discloses a barium device which includes lever means, barium supply means, valve means, piston means, squeeze bulb means and other components for providing a control system of barium in combination with air contrast for employment in the examination of patients.

Higuchi discloses an osmotic dispenser which includes a water-porous housing member confining a first flexible bag of relatively impervious material containing an active agent and provided with an active agent dispensing head and a second bag of controlled permeability to moisture containing a solution which exhibits an osmotic pressure gradient against water. A dual-compartment bag arrangement is illustrated in FIG. 4 and while the intended application and structure of such a dual-compartment bag arrangement is considerably different from the present invention, its general structure is of marginal relevancy.

Kline discloses a centrifuge tube formed from a transparent plastic and is provided at its bottom with a penetrable membrane through which an optical fiber element is passed upon completion of centrifuging of the contacts to enable visual observation of the effective light, particularly ultra-violet light, on the contents. The body of the centrifuge tube has an accordion-like configuration.

Schoenfeld et al. discloses a disposable douche comprised of a collapsible bellows forming a syringe and containing a premeasured amount of cleansing powder and an elongated dispensing nozzle adapted to be secured to an open end of the bellows.

Sneider ('662) discloses improvements in accordion-style containers used with syringes, douches, and the like. The improvements pertain to both prefilled, disposable, reusable syringe and douche containers and accessories used therewith.

Sneider ('332) discloses a liquid-filled sealable flexible bag having a manipulative discharge tube or nozzle. The FIG. 9 illustration of the invention discloses an accordion-like receptacle which is coupled to a tubular member.

Miller discloses a device for giving an enema which includes an inflatable balloon received on a pipe having an undulating outer shape. The pipe includes a groove which receives an air tube and although this air tube is exterior of the contrast medium passageway for a portion of its length, the end of the air tube is disposed within the tip opening where the contrast medium exits.

Pamplin et al. discloses a dental syringe for selective discharging of dry air, water or spray. The air tube is disposed within the water passageway for substantially the full length of the passageway. The free end is closed by the air tube and a branch passageway allows the delivery of water from this closed end.

Johnson discloses a method and apparatus for effecting medicinal treatment which includes two flow channels in side-by-side relationship extending from two separate storage chambers to a common delivery tip location.

SUMMARY OF THE INVENTION

An enema administering apparatus insertable into the rectum for delivery of a contrast medium to internal portions of a patient's anatomy according to one embodiment of the present invention comprises an enlarged tip portion having at least one contrast medium exit aperture located therein, and air passageway means external of the contrast medium passageway and having an air delivery outlet opening at a location adjacent the contrast medium exit aperture and adapter means by which the enlarged tip portion is assembled to the enema tube which delivers the contrast medium.

One object of the present invention is to provide an improved enema administering apparatus for double contrast studies.

Related objects and advantages of the present invention will be apparent from the following description.

BRIEF DESCRIPTION OF THE DRAWINGS

FIG. 11c is a partial, front elevation view of an alternative contrast medium storage reservoir and evacuating device.

FIG. 14 is a partial, fragmentary front elevation view of an enema tip and tube including an air passageway according to a typical embodiment of the present invention.

FIG. 14a is a perspective view of a flared air delivery tube compatibly arranged for use with the FIG. 14 enema apparatus.

FIG. 15 is a partial, fragmentary front elevation view of an alternative enema tip and tube arrangement also including an air passageway.

FIG. 16 is an exploded view of a tube retainer assembly compatibly arranged for use with the FIG. 15 enema apparatus.

FIG. 16a is a full section view of a tube retainer comprising a portion of the FIG. 16 assembly.

FIG. 25 is a partial, front elevation view in full section of an enema tip, adapter and enema tube assembly according to a typical embodiment of the present invention.

FIG. 26 is a partial, front elevation view in full section of an alternative enema tip, adapter, and enema tube assembly according to a typical embodiment of the present invention.

FIG. 27 is a partial, fragmentary front elevation view in full section of an alternative enema tip, adapter, and enema tube assembly according to a typical embodiment of the present invention.

FIG. 28 is a partial, front elevation view in full section of an enema tip including an air passageway and assembled to an adapter and enema tube and an air tube assembled to the tip.

DESCRIPTION OF THE PREFERRED EMBODIMENT

Figure 1:
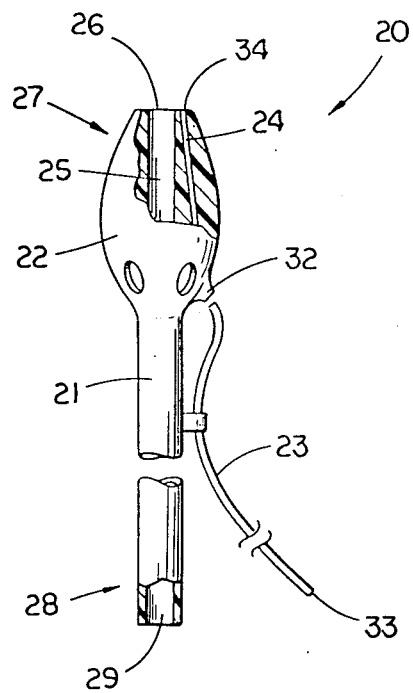
FIG. 1 is a partial, fragmentary front elevation view of an enema tip and tube including an air passageway according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated an enema administering apparatus 20 which includes an enema tube 21, an enlarged enema tip 22, air tube 23 and interior air passageway 24. Internal to enema tube 21 and enlarged enema tip 22 is a contrast medium passageway 25 which extends from a contrast medium discharge location 26 at inserted end 27 to a contrast medium inject location 29 disposed within free end 28.

Air tube 23 may be inserted into protuberance 32 with a press fit in order to couple air tube 23 to air passageway 24. Alternatively, interior air passageway 24 may be appropriately sized so that air tube 23 may be inserted through protuberance 32 into air passageway 24 and could conceivably even extend to a point beyond the outermost end of enema tip 22. In this particular arrangement, a source of air may be coupled to free end 33 of air tube 23 and with air tube 23 coupled to or inserted within air passageway 24, an overall air passageway from free end 33 to air delivery outlet opening 34 is provided. In this particular arrangement, air tube 23 is flexible and extends external to the enema stem (enema tube 21) yet is internal to the enema tip 22. It is important to note that the combined air passageway, including air tube 23 and interior air passageway 24, is external throughout its entire length to contrast medium passageway 25 and thus the flow of a contrast medium, such as barium, will not be impeded or interfered with by such air passageway or air tubing. Contrast medium passageway 25 is centrally positioned within tube 21 and tip 22 and is of a comparatively larger size (diameter) than air passageway 24.

These particular arrangements are well suited for double contrast studies wherein barium is first injected into the patient and preevacuation X-ray films are taken. Next the barium is evacuated, such as by suction means, and air is then introduced by means of the corresponding air tube and/or air passageway for the contrast postevacuation X-rays. Suitable means to retain the enema tip and the tube in position throughout such a fluoroscopy procedure are disclosed in my copending patent application Ser. No. 39,280, filed on May 16, 1979.

Figure 2:
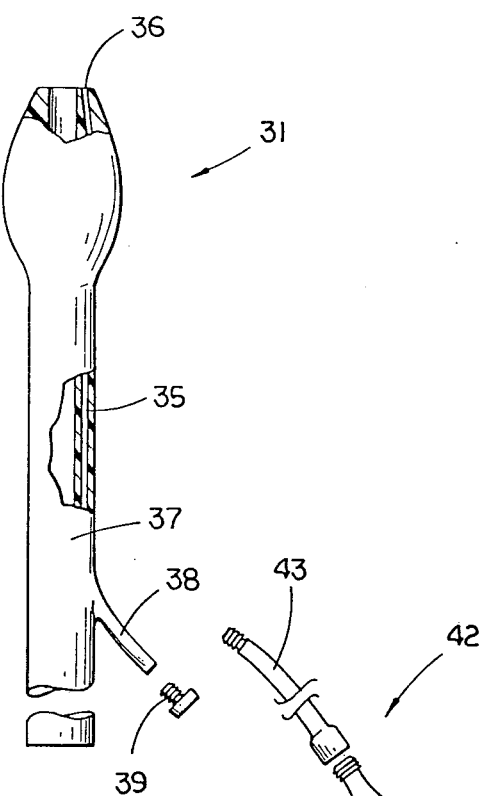
FIG. 2 is a partial, fragmentary front elevation view of an alternative enema tip and tube arrangement also including an air passageway.

Referring to FIG. 2, an alternative arrangement to the FIG. 1 apparatus is illustrated and the primary difference between alternative apparatus 31 and apparatus 20 is that interior air passageway 35 extends from air delivery outlet opening 36 down the length of enema tube 37 to protuberance portion 38 at which point air passageway 35 exits to the atmosphere. As is evident from this FIG. 2 illustration, the air passageway is completely contained within the enema tip and enema tube rather than exiting at the base of the enema tip as disclosed for apparatus 20. Apparatus 31 provides an alternative to the FIG. 1 arrangement even though the functioning of both arrangements are virtually the same.

Figure 2A:
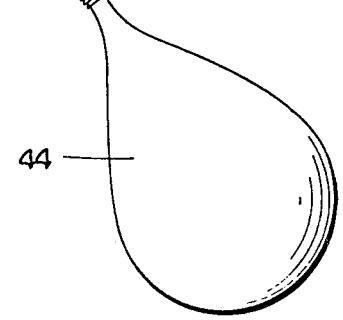
FIG. 2a is a perspective view of an air-bulb and tube arrangement suitable for air introduction into an air passageway.

Protuberance 38 is provided with a closure plug 39 so that apparatus 31 may be used in a conventional manner when double contrast studies are not called for. When air is desired to be incorporated as part of the study, plug 39 is removed and an air introduction device 42 (see FIG. 2a) is coupled to protuberance 38. Air introduction device 42 includes a connecting tube 43 and an air-bulb 44. The separable nature of tube 43 and air-bulb 44 enables different lengths of tubing and different bulb sizes to be used, depending upon the particular circumstances and the particular patient.

Figure 3:
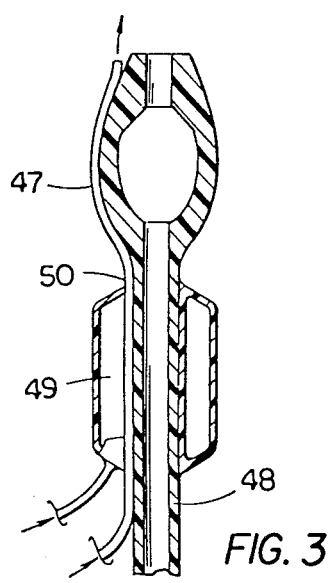
FIG. 3 is a partial, fragmentary front elevation view of yet another alternative enema tip and tube arrangement also including an air passageway.
Figure 4:
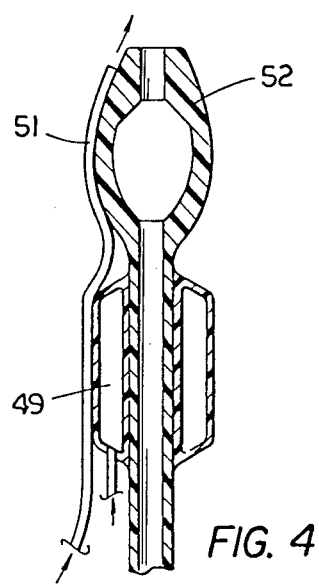
FIG. 4 is a partial, fragmentary front elevation view of still another enema tip and tube arrangement also including an air passageway.

One particular style of enema administering apparata includes the providing of an annular element formed of a resilient, flexible material. Such an arrangement is fully disclosed in my U.S. Pat. No. 3,459,175 issued Aug. 5, 1969. In this patented arrangement, the air tube passes between the enema tube and the surrounding resilient, flexible annular element, enters the enema tip at its base and exits interior to the contrast medium discharge location (such as 26). The FIG. 3 and FIG. 4 illustrations represent alternative arrangements to this patented configuration wherein the air tube is moved external to the enema tip rather than being internal to the tip. This change is important in that the air tube will not block or otherwise interfere with the delivery of the contrast medium to the patient. Nor is there the likelihood that the air tube will become clogged with barium or other material as part of the barium introduction into the patient or the evacuation of the barium from the patient.

Referring to FIG. 3, air tube 47 is disposed between enema tube 48 and annular element 49. As is disclosed in U.S. Pat. No. 3,459,175, which is hereby expressly incorporated by reference, air tube 47 lays within a groove longitudinally extending along the length of enema tube 48 such that inflation of annular element 49 will not close or shut off the air passageway through tube 47. Exit location 50 designates that point at which air tube 47 exits from between annular element 49 and tube 48. Thus from exit location 50 on upward toward the outermost end of the enema tip, a groove is not necessary. However, as is illustrated in FIG. 4a, a groove disposed within the enema tip is envisioned and would be suitable to reduce the overall size of the enema tip portion which is inserted into the patient's rectum.

An alternative arrangement to the use of a groove along the length of enema tube 48 would be to arrange annular element 49 with a rigid internal wall, contiguous with the outside diameter of enema tube 48, yet providing clearance for air tube 47. Thus air inflation of annular element 49 only exerts pressure in an outwardly direction and does not cause compression of or closing off of air tube 47. FIG. 4 illustrates yet another alternative arrangement wherein the air tube 51 is disposed external to annular element 49 as well as external to enema tip 52. This particular alternative arrangement is intended to function in much the same manner as the arrangement disclosed in FIG. 3 and the use of a groove 53 in enema tip 52 is equally applicable to the FIG. 4 arrangement as it was to the FIG. 3 arrangement. The remaining components of an enema administering apparatus so that disclosed by FIGS. 3 and 4 is similar to that taught by U.S. Pat. No. 3,459,175 as well as by my copending patent application Ser. No. 39,280, filed on May 16, 1979.

Figure 5:
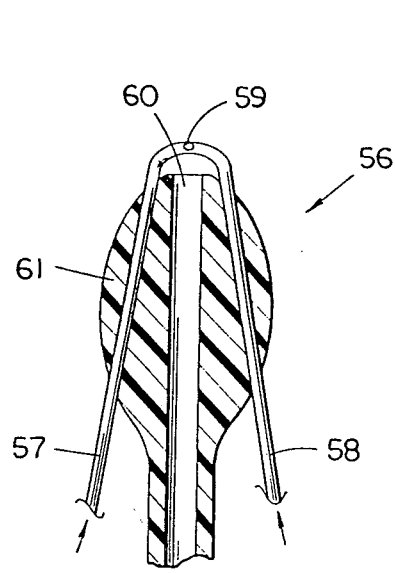
FIG. 5 is a partial, fragmentary front elevation view of yet another alternative enema tip and tube arrangement including dual air passageway means.
Figure 5A:
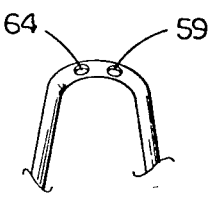
FIG. 5a is a partial perspective view of an alternative dual air passageway arrangement suitable for use with the FIG. 5 alternative arrangement.

Referring to FIG. 5, there is yet another alternative arrangement illustrated wherein a dual branch air tube 56 is disclosed having a first air inlet branch 57 and a second air inlet branch 58, each of which are connected together and include an air exit or delivery outlet opening 59 disposed adjacent to contrast medium discharge location (exit aperture) 60 located in the outermost end of enema tip 61. This particular dual-branch air tube arrangement is desirable when there is a likelihood that one or the other of the two air inlet branches may become choked or closed off and thus a backup or secondary air introduction passageway is necessary. This particular arrangement is also suitable for use with the air introduction apparatus of FIG. 10 in that there is a single supply source of air and two air tubing branches which are joined with the source by means of a suitable valve. This particular arrangement will be discussed in greater detail hereinafter. Another modification envisioned to the FIG. 5 dual branch air tube arrangement is to provide a second air exit or air delivery outlet opening 64 spaced apart from outlet opening 59 so that if one or the other of these two outlet openings becomes clogged with contrast medium or other foreign matter, there will be a second or backup outlet opening for delivery of the air.

Figure 4A:
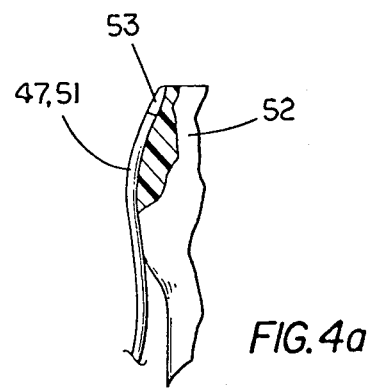
FIG. 4a is a partial, fragmentary front elevation view of a side groove within the FIG. 4 enema tip with air tubing means disposed therein.
Figure 6:
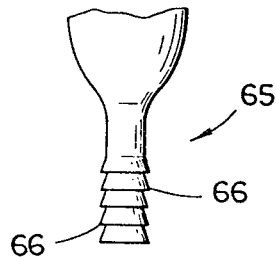
FIG. 6 is a partial, front elevation view of an enema tip suitable for press-fit connection with an enema tube.
Figure 7:
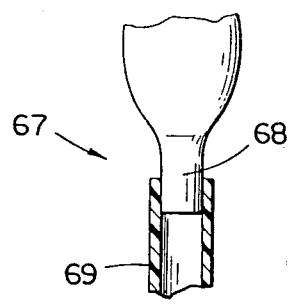
FIG. 7 is a partial, fragmentary front elevation view of an enema tip press-fit into an enema tube.

Inasmuch as some of the various arrangements and alternatives described so far may only involve modification of the enema tip portion, such as the air passageway of FIG. 1 and the groove of FIG. 4a, it is possible to construct the enema tips as replaceable, interchangeable units such that the remainder of the enema administering apparatus may remain unchanged. In order to create such replaceability enema tip 65 (see FIG. 6) is provided with a series of serrations 66 disposed on its free end which are of a style and arrangement commonly found such that a resilient flexible tubing member may be axially pressed over such serrations and thus provide a secure and tight connection therewith. Alternatively, (see FIG. 7) enema tip 67 may be arranged with a free end 68 of an outside diameter size which is slightly larger than the inside diameter size of tubing 69 such that the tubing is forced to expand outwardly when force-fit over free end 68. This arrangement also provides a tight connection between the enema tube and enema tip.

Figure 8:
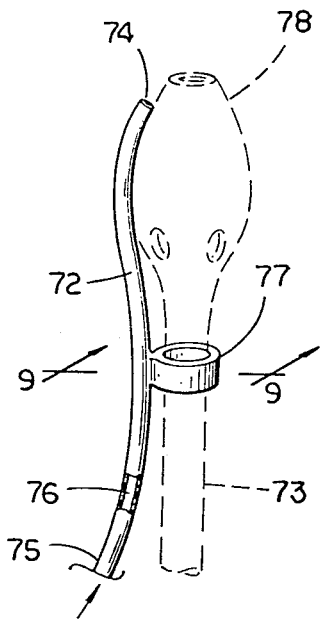
FIG. 8 is a perspective view of an air tube arrangement including cuff means for retaining an enema tube.
Figure 9:
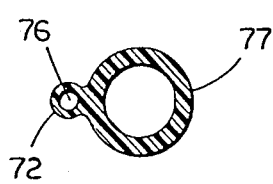
FIG. 9 is a section view of the FIG. 8 air tube and cuff arrangement as taken along line 9—9 in FIG. 8.

Referring to FIG. 8, there is illustrated yet another arrangement in which the air tube is disposed completely external of both the enema tube and enema tip. Air tube 72 extends along the length of enema tube 73 from an air delivery outlet opening 74 at the inserted end to an air inlet opening at end 75. The air inlet opening at end 75 is able to be connected to a source of air, such as air-bulb 44, in order to provide air from end 75 through air passageway 76 to air outlet opening 74 at a location adjacent the enema tip. Joined to the outside diameter of air tube 72 is a collar member 77 which has a circumferential size suitable to surround the outside diameter of enema tube 73 with a snug fit in order to hold air tube 72 in a particular desired orientation relative to enema tube 73 and enema tip 78. By fabricating collar member 77 out of a somewhat flexible or resilient material, enema tip 78, although enlarged over enema tube 73, is able to be forced through collar member 77 and since enema tube 73 is slidably received within collar member 77, the position of air outlet opening 74 with respect to the contrast medium discharge location can be controlled. FIG. 9 is a section view through both air tube 72 and collar member 77 in the direction of cutting line 9—9 and is sectioned for plastic or similar synthetic material.

Figure 10:
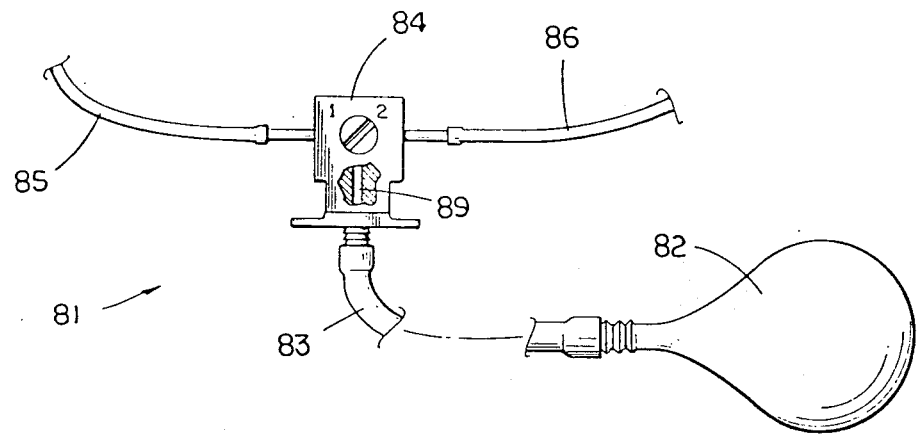
FIG. 10 is a partial perspective view of an air-introducing arrangement including valve means and a dual air passageway.

Referring to FIG. 10, there is illustrated an air introduction device 81 which includes an air bulb 82, connecting tube 83, air valve 84, first air tubing branch 85 and second air tubing branch 86. By compression of air-bulb 82, air is introduced through connecting tube 83 into air valve passageway 89. At this point, the selected orientation of air valve 84 governs whether the air within passageway 89 is directed through first air tubing branch 85 or through second air tubing branch 86 or through both. The incorporation of two air tubing branches provides a dual system as well as a backup system in the event one or the other of these two branches would become closed off or restricted in some manner. This particular air introduction device is particularly well suited to those enema tube and enema tip designs which incorporate a dual-air passageway such as the arrangement of FIG. 5.

Figure 11:
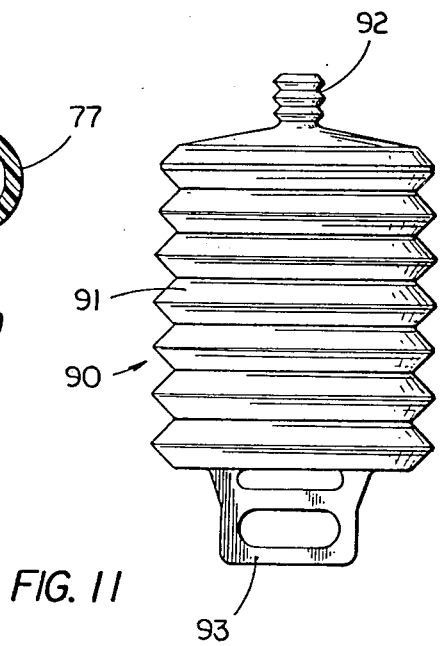
FIG. 11 is a front elevation view of a contrast medium storage reservoir and evacuating device.
Figure 11A:
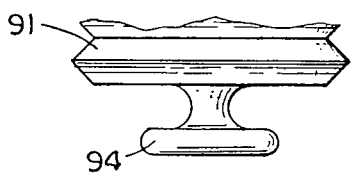
FIG. 11a is a partial, front elevation view of one handle style suitable for use with the FIG. 11 device.
Figure 11B:
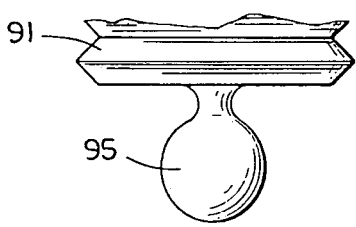
FIG. 11b is a partial, front elevation view of another alternative handle design suitable for use with the FIG. 11 device.

Referring to FIGS. 11, 11a, 11b and 11c, there is illustrated a contrast medium introduction apparatus 90 which includes a contrast medium storage reservoir 91, a combination filling port and discharge port 92 and a centrally positioned handle 93 located at the opposite end from combination port 92. Once a suitable contrast medium, such as barium, is introduced into storage reservoir 91 by means of filling port 92, this contrast medium is then in a loaded position ready for introduction into a patient. The externally threaded outside diameter of filling port 92 provides a suitable connection means to an enema tube or similar tubing arrangement. Once filling port 92 is connected to such a tube or tubing arrangement and the enema tip is rectally inserted into the patient, compression of storage reservoir 91 by the exertion of pressure through handle 93 in the direction of filling port 92 causes the contrast medium within storage reservoir 91 to be discharged out of discharge port 92. The accordion-like configuration of storage reservoir 91 and the symmetrical and centrally disposed locations of filling port/discharge port 92 and handle 93 provide a virtually complete discharge of the contrast medium from storage reservoir 91. FIGS. 11a and 11b represent alternative handle styles to that of handle 93. The FIG. 11a handle 94 is a generally disclike member with a reduced diameter at its point of connection to storage reservoir 91, and the FIG. 11b representation is of a generally spherical handle 95 whose point of attachment to storage reservoir 91 also includes a reduced diameter portion. FIG. 11c illustrates an alternative arrangement for the filling port-/discharge port 92a. Apparatus 90a is configured with such a combination port 92a which is of comparatively larger size than port 92 of FIG. 11.

Figure 13:
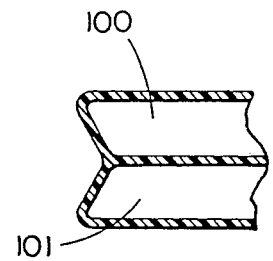
FIG. 13 is a front elevation section view of the FIG. 12 introduction device as taken along lines 13—13 in FIG. 12.
Figure 12:
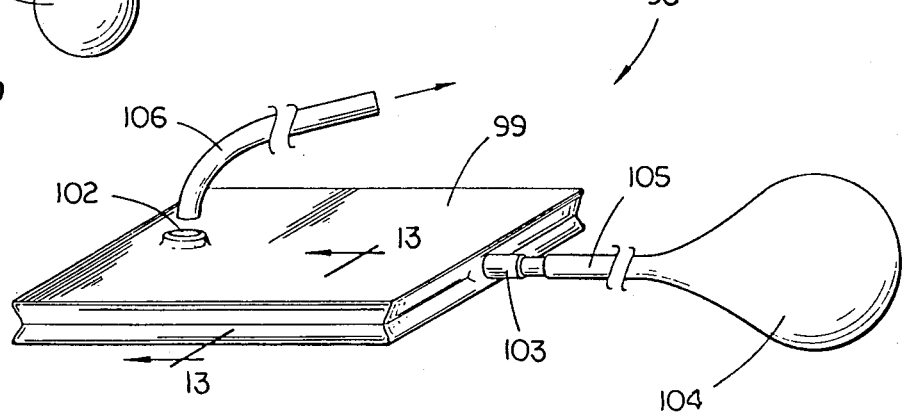
FIG. 12 is a perspective view of a contrast medium introduction device.

Referring to FIGS. 12 and 13, there is illustrated yet a further contrast medium introduction apparatus 98 which includes a main pouch member 99 divided into an upper compartment 100 and a lower compartment 101 (see FIG. 13). Upper compartment 100 is provided with a contrast medium discharge port 102 which may also serve as a filling port similar to the dual purpose filling port/discharge port 92. Lower compartment 101 is provided with an air connection tube 103 which may be suitably connected to an air-bulb 104 by means of a variable length of tubing 105. This particular contrast medium introduction apparatus is suitable for introduction of a contrast medium such as barium from a remote location. By increasing the overall length of tubing 105, air-bulb 104 may be placed in a location adjacent to the X-ray technician or radiologist while the main pouch 99 is in close proximity to the patient. Then by compression or depression of air-bulb 104, lower compartment 101 is inflated and as this inflation occurs, pressure is applied on upper compartment 100 reducing its volumetric size and forcing the contrast medium stored therein to be discharged or expelled by means of tubing 106. Tubing 106 may be an enema tube or may be connected to an enema tube, and by such tubing the discharged contrast medium is ultimately injected into the patient. In order to achieve this particular result, it is important that the material utilized to fabricate main pouch 99 and thus upper and lower compartments 100 and 101, respectively, be a flexible, resilient material.

Patient comfort is of concern and importance in the design of enema devices, and although protuberance 32 (see FIG. 1) is located in a noninterfering manner below and inside of the larger-diameter surface of tip 22, not all tip designs are ideally configured for patient comfort. For example, if the air exit location was at some intermediate point on the side surface of the tip rather than the end, and if an air tube was employed, then the location of the free end of the air tube would be of concern. Clearly, it is desirable to configure the tips such that they can be used for double contrast studies or not used for such studies as the physician desires. If a double contrast study is desired, often one end of the air tube is merely inserted into the enema tip air passageway and the other end is coupled to a source of air. However, any dimensional shift or relocation of the air tube outwardly from the surface of the tip presents an abrasive edge to the interior tissue of the patient and can cause discomfort.

FIGS. 14 and 14a illustrate an enema tip 120 and air tube 121 construction which provide at least two very important advantages to conventional enema apparata. First, the cooperating design of these two components insures a smooth, flush fit of the end of the air tube relative to the exterior surface of the tip. Secondly, if the contrast medium (barium) tube 122 becomes separated from tip 120, leaving the tip in the patient, air tube 121 is able to be used to easily extract the tip.

Enema tip 120 includes a centrally located barium passageway 123 and an air tube passageway 124 which is completely exterior of passageway 123 and is countersunk at its distal end 125. Air tube 121 is of a predetermined length and is substantially straight throughout its entire length with a conical-shaped (flared) end 128. The angular pitch and diameter size of flared end 128 is compatible with the countersunk configuration of distal end 125 such that the flared end fits within the distal end in a flush-to-recessed arrangement. It should be clear that if tip 120 becomes separated from tube 122, tube 121 can be used to pull tip 120 free of the patient by pulling on end 129. It is also end 129 to which a source of air is connected for injection of air as part of the double contrast study.

Flared air tube 121 may also be used in a unique manner even with enema tips which do not have the corresponding countersunk end on the air tube passageway. Referring to FIG. 15, which is similar in certain respects to the enema tip structure of FIG. 2, enema tip 130 and tube 131 include an air tube passageway 132 which is disposed substantially parallel to contrast medium (barium) passageway 133. Passageway 133 is comparatively larger than air tube passageway 132 and is centrally located within both the tip and tube. Tube 131 includes an outwardly angled protuberance 134 which is internally threaded (see FIG. 16) at its free end. This threaded fitting enables the connection of a tube-retaining assembly 137 to the protuberance. Assembly 137 includes a hollow tube retainer 138 which is externally threaded at first end 139 and internally threaded at opposite end 140. Assembly 137 also includes a hollow retainer cap 141 which is externally threaded at one end for engagement with end 139 of the tube retainer.

Figure 21:
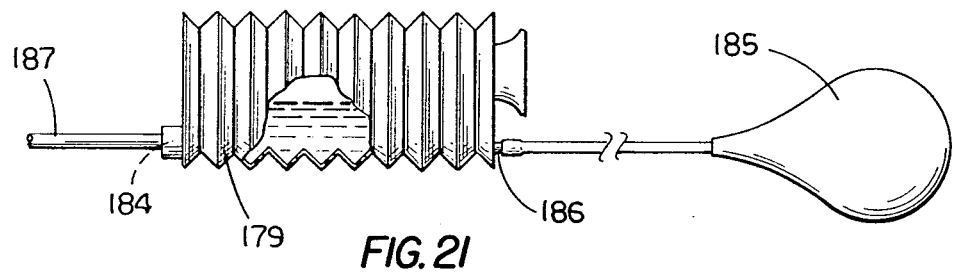
FIG. 21 is a fragmentary, side elevation view of the FIG. 19 device as arranged for contrast medium delivery.

Continuing with reference to the detail of FIG. 16, the positional relationship of protuberance 134, retainer 138 and hollow retainer cap 141 are illustrated. The detail of FIG. 16a is a full section view of the retainer and illustrates the presence of a countersunk surface 144 centered around tube opening 145. Surface 144 is compatibly sized in diameter and angular pitch to receive the flared end 128 of air tube 121. Consequently, by first inserting end 129 into retainer 138 and advancing the tube to a position of abutting contact of flared end 128 with surface 144, the air tube will be at its maximum extension into tip 130. Then, as cap 141 is threaded into place and tip 146 projects into the center of the countersunk surface toward opening 145, air tube 121 is locked in position. Since tip 146 is hollow, an air flow path is maintained from end 147 of cap 141 through to hole 148 in tip 130. With this configuration, a predetermined length for tube 121 is an important consideration so that end 129 will not extend beyond the end of hole 148 where it could irritate the patient. Connection of a source of air to end 147 may be achieved by a variety of structures including, but not limited to, those illustrated in FIGS. 2a, 10 and 21.

Wile considerations of patient comfort, ease of operation, adaptability and versatility are important in the design of enema apparata, there remain other important factors such as the reliability of the apparatus and how well it works. One area of importance is the retention of the enema tip in the patient. My U.S. Pat. No. 3,459,175 issued on Aug. 5, 1969 and my copending U.S. patent application Ser. No. 39,280 filed on May 16, 1979 disclose various retention means for enema apparata. U.S. Pat. No. 3,459,175 discloses an annular element which operates much like a balloon and is positioned around the enema tube. When inflated, this element enlarges and closes off the point of entry into the patient of the enema tip and tube and thereby prevents any barium from being discharged prematurely. This annular element also has certain retention capabilities depending upon its precise manner and location of use.

Figure 17:
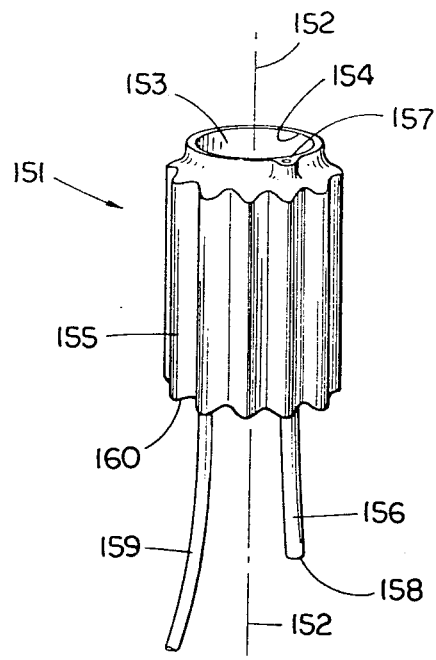
FIG. 17 is a perspective view of an inflatable annular element compatible for use with various enema tip and tube configurations of the present invention.

These types of annular elements are typically of a cylindrical shape in order to be effective over a greater distance of longitudinal travel relative to their inflated diameter size. At the time of insertion, the annular element is collapsed and the case of insertion is directly related to the size of the element. FIG. 17 illustrates an annular element concept which includes as part of its construction an air tube for use with double contrast studies. Annular element 151 is generally cylindrical and has a pleated or corrugated configuration with the longitudinal axis of the corrugations extending substantially parallel to centerline 152 of the enema tube-receiving aperture 153. Element 151 includes an inner wall 154 which defines aperture 153 and a flexible outer enclosing skin 155 defining an interior void. Skin 155 is the portion that is corrugated and air tube 156 is disposed in the interior void adjacent inner wall 154 and this tube terminates at edge 157. The free end 158 of air tube 156 is used for connection to a supply source of air. Inflation tube 159 is connected to lower edge 160 and opens into the interior void for inflation of element 151. During the inflation of element 151, skin 155 expands outwardly thereby making contact with the patient's surrounding tissue and walls.

The FIG. 17 illustration can be considered similar in some regards to FIG. 3, and it is to be noted that the air tube 47 of FIG. 3 extends through annular element 49 and lays beside the exterior of the enema tip. As has been discussed above, one arrangement possible is to extend the air tube through a passageway in the tip thereby leaving the exterior size and shape of the tip unaffected. The embodiment of FIGS. 14 and 15 focus on this concept and the advantages of the associated flared air tube of FIG. 14a have previously been discussed. The enema tip and tube construction of FIG. 14 is suitably arranged for use with annular element 151. If flared air tube 121 is also used, its path is first through passageway 124 and then through air tube 156.

The corrugated construction of element 151 enables a more compact, collapsed size than what is achievable with true cylindrical annular elements. The result of this more compact (smaller) size is that there is greater ease of insertion and less discomfort to the patient. The configuration of FIG. 17 is molded as a single, integral member out of a synthetic material, such as one of the various thermosetting or thermoforming plastics. The design is particularly well suited as an option which the physician can either slide onto the enema tube and use or not use as he elects. The almost universal adaptability means that its uses are not restricted to one particular enema tip and tube manufacturer nor to any one particular style.

Figure 18:
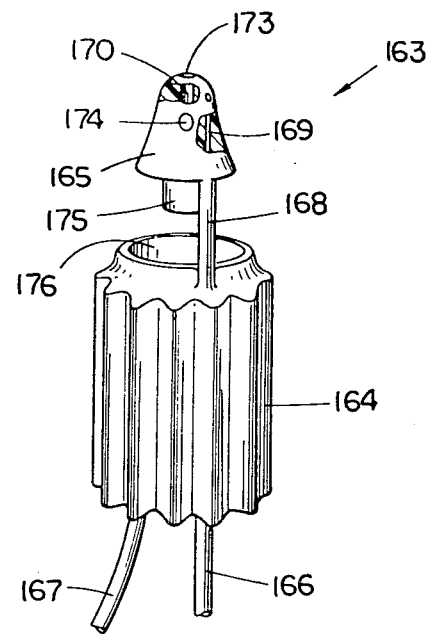
FIG. 18 is a perspective view of a combination inflatable annular element and enema tip which is arranged for connection to a contrast medium flow tube in accordance with a typical embodiment of the present invention.

Referring to FIG. 18, there is illustrated a further extension of the concept and structure disclosed by the annular element of FIG. 17. Enema tip subassembly 163 includes a corrugated, inflatable annular element 164, an enema tip 165, an air tube 166, and an element inflation tube 167. Air tube 166 extends through element 164 and includes a connecting portion 168 which attaches to tip 165 and provides a continuous, axially aligned air flow passageway including air passageway 169 which is located in the enema tip. Tip 165 includes a flow passageway 170 for the contrast medium (barium) which terminates at opening 173 and may optionally include additional flow exit openings such as, for example, opening 174. The enlarged end (base) of tip 165 is provided with a centrally located tubular fitting 175 which is substantially concentric around flow passageway 170.

Fitting 175 provides the connection means for a barium delivery tube. The method of connection is a press-fit and fitting 175 may optionally be of a serrated design (similar to FIG. 6) to enhance the tightness and reliability of the press fit. By sizing fitting 175 to fit snugly within the connecting tube for barium deliver and by sizing aperture 176 to fit snugly around the outside diameter of the connecting tube, a complete enema assembly is created. Similar to the construction of FIG. 17, subassembly 163 is molded as a single, integral member out of a suitable synthetic material. This single member construction greatly reduces the time and effort normally expended to assembly a variety of piece parts together in order to begin the fluoroscopy examination. With the disclosed subassembly, the physician or technician or nurse merely needs to connect the barium flow tube and the sources of air to tubes 166 and 167 and begin the procedure. There is no requirement to locate several parts nor to assure that the specific parts selected are all compatible with one another for a proper fit. Similarly, there is no need to inventory or store a wide variety of piece part mixtures, "one size fits all."

At this point, it is necessary to regress for a moment and redirect consideration to the apparatus disclosed in FIG. 10. By use of air valve 84, the flow direction of air can be controlled through either branch. By coupling tube branch 85 to tube 167 (FIG. 18) and branch 86 to tube 166, the selective use of air bulb 82 and air valve 85 enables the physician to first inflate annular element 164 and thereafter conduct a double contrast study introducing air through the other branch when required. If either step, but not both, is performed solely, then air valve 84 remains in a fixed orientation and air is delivered through only one branch. The FIG. 10 arrangement is also suitable for use with the FIG. 17 annular element and air delivery tubing as well as with related devices which have a requirement for two separate sources of air flow.

Figure 19:
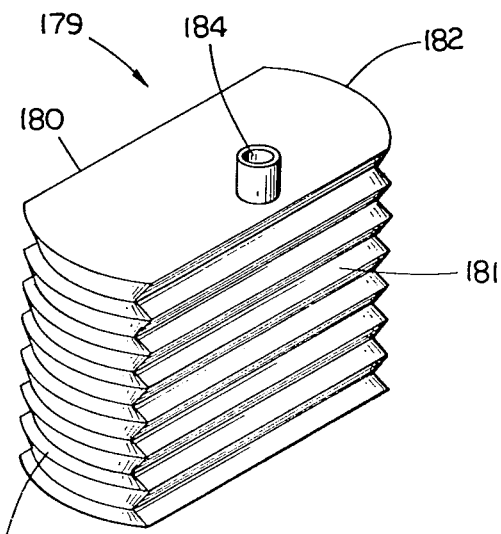
FIG. 19 is a perspective view of a contrast medium storage reservoir and evacuating device according to a typical embodiment of the present invention.
Figure 20:
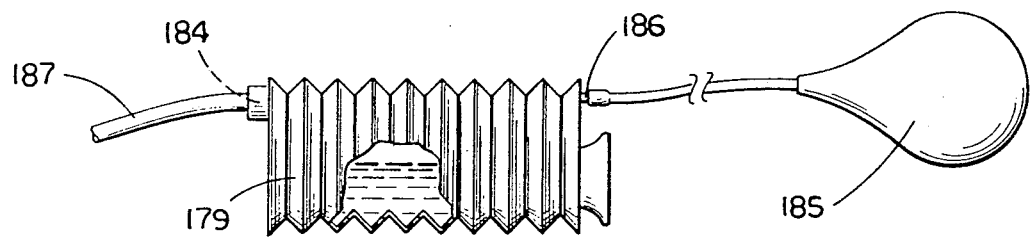
FIG. 20 is a fragmentary side elevation view of the FIG. 19 device as arranged for air delivery.

Referring to FIG. 19, there is illustrated a novel apparatus for selectively introducing either a contrast medium (barium) or air and for removal of the contrast medium by a suction force. Apparatus 179 is configured with a collapsible, accordion-like shape which is substantially straight (flat) on two opposite sides 180, 181 and curved on the two intermediate sides 182, 183. The substantially straight sides allow the apparatus to be oriented in a horizontal position (see FIGS. 20 and 21).

Flow port 184 is centrally located between the curved sides, but is offset from the centerline toward side 181. With apparatus 179 disposed in a horizontal orientation, resting on side 180 (FIG. 20), the flow port is nearer the top of the apparatus. With apparatus 179 reversed as to its horizontal orientation (see FIG. 21), flow port 184 is nearer the bottom of the apparatus. Prior to use, apparatus 179 is partially filled with a contrast medium and hand pump 185 is used to introduce air into the interior of the apparatus. When apparatus 179 is oriented as in FIG. 20, the introduction of air flows from inlet 186 to flow port 184 and out through hose 187. Alternatively, when the apparatus is reversed, the incoming air creates a pressure head over the barium which causes the barium to flow out hose 187.

Figure 22:
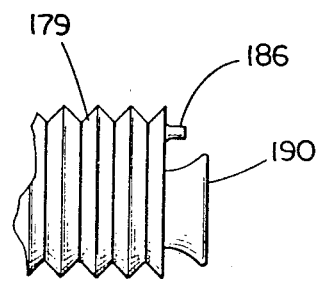
FIG. 22 is a partial side elevation view of one handle style suitable for use with the FIG. 19 device.

Referring to FIG. 22, one end of apparatus 179 is illustrated in greater detail. Attached as part of this end is a handle member 190 which has an undercut area adjacent the end surface for easier gripping. Handle member 190 is particularly well suited for compressing and extending the body of the apparatus (collapsing or opening the accordion) for pumping barium into the patient and suction removal of the barium from the patient. If manual force, is going to be used for collapsing the accordion shape in lieu of using the hand pump for barium introduction, inlet 186 is closed. The removable nature of hose 187 from flow port 184 allows for the easy filling and cleaning of the apparatus.

Figure 23:
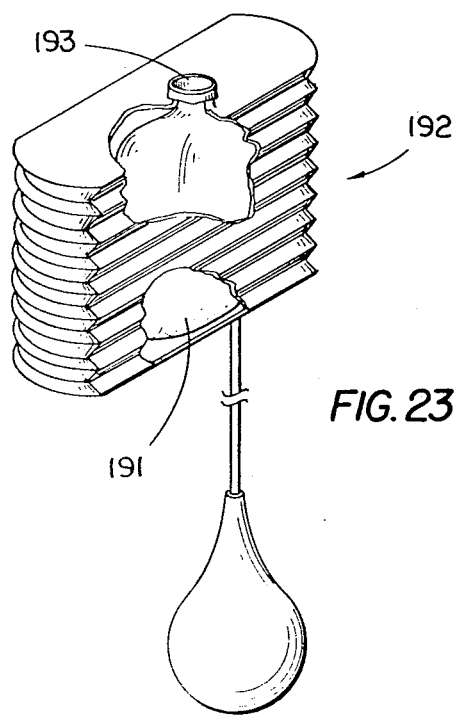
FIG. 23 is a fragmentary perspective view of a contrast medium introduction device including an inner bag and outer enclosure construction.

The main body portion of apparatus 179 which has the accordion-like shape is hollow throughout its interior and is sealed closed between flow port 184 and inlet 186. An alternative construction is disclosed by FIG. 23 wherein a collapsible contrast medium bag 191 filled with a contrast medium is disposed within apparatus 192 and is interiorly connected to flow outlet port 193. The opposite end includes an inlet and hand pump similar to apparatus 179. An air is introduced, the air pressure compresses bag 191 causing the contrast medium to flow out through port 193. The collapsible bag is able to be refilled by connection of a source of contrast medium and reintroduction under slight pressure.

Figure 24:
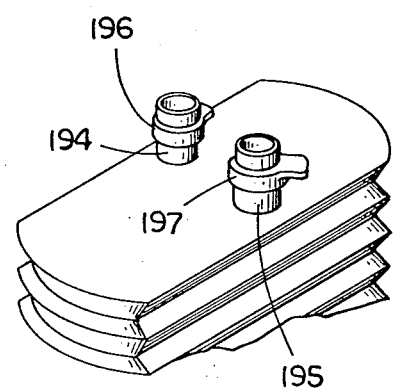
FIG. 24 is a partial perspective view of an alternative configuration for the FIG. 23 device including control valve means.

Alternatively, it is envisioned that an additional flow outlet may be placed in the end of the apparatus (see FIG. 24) and that each exit port, port 194 for air and port 195 for contrast medium (via an interior collapsible bag) be fitted with control valves 196 and 197, respectively, for selecting what type of flow is desired.

Referring to FIG. 25, there is illustrated an enema administering apparatus 243 which includes an enema tip 200, a connecting adapter 201 and an enema tube 202. The enema tip 200 is coupled in flow communication with the connecting adapter and is securely held in place by ridges 204 disposed on the exterior of the adapter. Similarly, the enema tube 202 is coupled with the opposite end of the connecting adapter flow and securely held in place by ridges 203.

FIG. 26 illustrates an emena administering apparatus 244 which includes an emena tip 205, a connecting adapter 206 and an enema tube 207. As in FIG. 25, the tip 205 is coupled with the adapter 206 and securely held in place by ridges 209 disposed on the exterior of the adapter. Similarly, the opposite end of the adapter is coupled with the enema tube 207 and is held securely in place by ridges 208 also on the exterior of the adapter.

FIG. 27 illustrates yet another enema administering apparatus 245 which includes an enema tip 210, a connecting adapter 211, and an enema tube 212. The tip 210 and adapter 211 are coupled together in flow communication and are held securely in place by ridges 213 on the interior of the adapter. The adapter 211 and enema tube 212 are also flow coupled together and held securely by ridges 214 also on the interior of the adapter.

FIG. 28 illustrates an enema administering apparatus 246 which includes an enema tip 215, connecting adapter 217, an enema tube 218 and an air tube 221. The tip 215 includes an air passageway 216. The tip 215, adapter 217 and enema tube 218 are coupled and held together in a manner virtually identical to the embodiment of FIG. 25. The air tube 221 is coupled to the tip's air passageway 216 in order to provide for a flow of air for double contrast studies. With regard to the air passageway 216 and air tube 221, these may be provided as part of the FIG. 26 and FIG. 27 embodiments as well.

Figure 29:
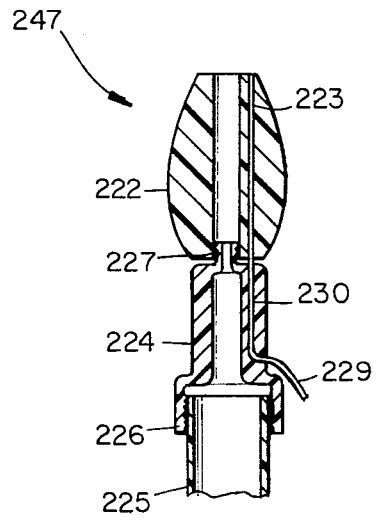
FIG. 29 is a partial, front elevation view in full section of an enema tip including an air passageway and assembled to an adapter which also includes an air passageway.

FIG. 29 illustrates an enema administering apparatus 247 which includes an enema tip 222, connecting adapter 224 and air tube 229. The tip 222 has an air passageway 223 and the adapter includes communicating air passageway 230. The enema tip 222 is coupled to adapter 224 so that the air passageways 223 and 230 are aligned in flow communication with each other. The adapter 224 and tip 222 are held together securely by adapter ridges 227 at one end, and adapter 224 is securely coupled with enema tube 225 by means of adapter ridges 226 at the opposite end of the adapter. Air tube 229 is coupled in flow communication with the adapter's air passageway 230.

FIGS. 25-29 illustrate that through the use of various adapters 201, 206, 211, 217 and 224 it is possible to use various tips 200, 205, 210, 215 and 222 with different sizes of enema tubing 202, 207, 212, 218 and 225. This ability to interchange tips and tubing via the adapter permits a single tip to be used with virtually any size of tubing and thereby allows the physician to construct a tip and tube assembly for each patient. For double contrast studies, a tip such as 215 or 222 can be used because of the presence of air passageways 216 or 223. The adapter can be arranged either with an air passageway that couples to the tip or without as in FIG. 28.

With this limited but illustrative array of possibilities, it is easy to see how useful adapters would be. There are various other configurations of adapters that could be employed, and also various other methods to achieve the coupling. The basic principle is that an assortment of inexpensive and easy-to-apply adapters afford the physician the possibility of combining any tip with any tubing in order to administer enemas and conduct double contrast studies.

Figure 30:
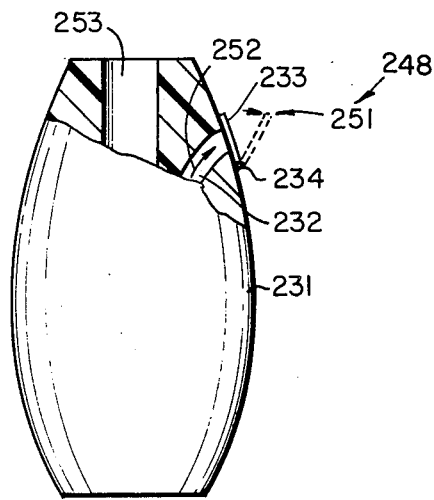
FIG. 30 is a partial, fragmentary front elevation view of an enema tip including an air passageway valve cover and hinge.

FIG. 30 illustrates the tip portion 231 of an enema-administering device 248 which includes an air passageway 232 and an air passageway cover 233. The cover 233 is disposed in a normally closed condition and is maintained in such fashion by living hinge 234. The flow of air through passageway 232 as represented by arrow 252 pivots the cover 233 outwardly to an open position as indicated by broken line 251. Cover 233 and hinge 234 form a type of air valve means which may be easily molded as part of the tip or onto the end of an air tube. When the contrast medium is evacuated through the contrast medium passageway 253 the contrast medium cannot flow into the air passageway because it is closed by cover 233. However, when air is forced through the air passageway, the cover 233 is moved to an open condition allowing air to enter the patient. This air valve concept alleviates many of the problems associated with double contrast studies that are caused by the clogging of the air passageway with contrast medium.

Figure 31:
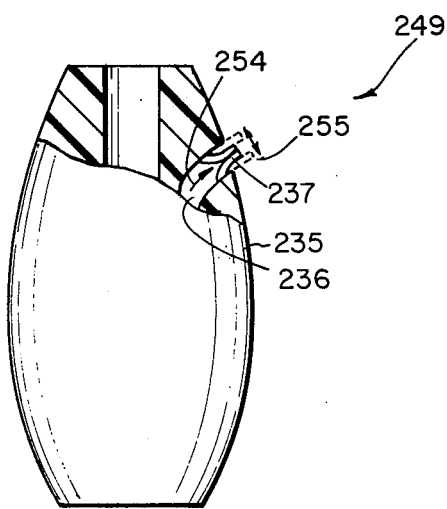
FIG. 31 is a partial, fragmentary front elevation view of an enema tip including an air passageway which includes a pair of normally closed flexible lips.

FIG. 31 illustrates a portion of an enema administering device 249 which includes an enema tip 235, and an air passageway 236 and a set of flexible lips 237. The lips are disposed in a normally closed condition and they are actuated by the flow of air through air passageway 236. The air flow is represented by arrow 254 and the open position of the lips is represented by broken lines 255. This arrangement provides virtually the same advantages as the FIG. 30 embodiment, and other valve styles could also be used.

Figure 32:
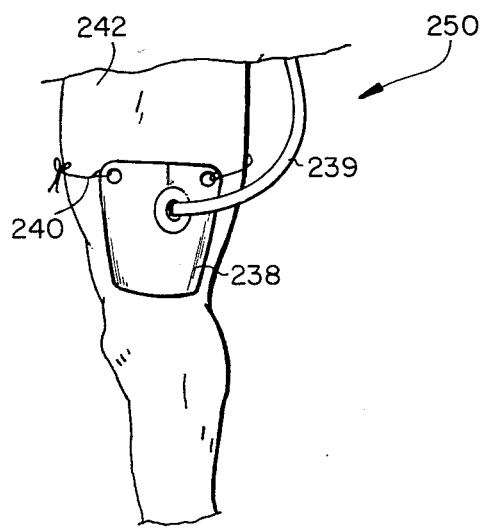
FIG. 32 is a partial, fragmentary side elevation view of a patient's leg with a barium bag attached thereto.

FIG. 32 illustrates an enema administering device 250 which includes a contrast medium bag 238 which includes an enema tube 239 and attaching means 240. The attaching means are used to secure the bag 238 to the patient's leg 242. The bag can be tied around leg of the patient 242 as is illustrated or alternatively, the bag may be secured by straps, snaps or "Velcro." With a shortened enema tube 239 and small bag 238, this leg-attaching location solves all the concerns earlier expressed as to what to do with the bag when it is time to drain the contrast medium.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An enema administering apparatus insertable into the rectum for delivery of a contrast medium to internal portions of a patient's anatomy, said enema administering device comprising:

an enlarged tip portion including a contrast medium passageway and air passageway mans disposed external of said contrast medium passageway and having an air delivery outlet opening; and valve means disposed adjacent to said air delivery outlet opening and adapted for regulating the flow into and out of said air passageway means.

2. The enema administering apparatus of claim 1 wherein said valve means comprises a normally closed, air-flow-actuated damper.

3. The enema administering apparatus of claim 1 which said valve means comprises a pair of normally closed, air-flow-actuated flexible lips.

* * * * *